United States Patent
Giordano

(10) Patent No.: US 6,180,333 B1
(45) Date of Patent: Jan. 30, 2001

(54) DETERMINATION OF CYCLIN-DEPENDENT KINASE INHIBITOR P27 LEVELS AS A PROGNOSTIC FACTOR IN CANCER PATIENTS

(75) Inventor: Antonio Giordano, Philadelphia, PA (US)

(73) Assignee: Thomas Jefferson University, Philadelphia, PA (US)

(*) Notice: Under 35 U.S.C. 154(b), the term of this patent shall be extended for 0 days.

(21) Appl. No.: 09/078,422

(22) Filed: May 14, 1998

Related U.S. Application Data
(60) Provisional application No. 60/046,529, filed on May 15, 1997.

(51) Int. Cl.$^7$ .............................. G01N 33/53; C12Q 1/68; C12Q 1/00; C07K 14/47; C07K 16/18

(52) U.S. Cl. .............................. 435/4; 435/7.1; 435/7.23; 435/7.21; 435/967; 435/960; 436/501; 436/503; 436/811; 530/387.1; 530/389.1; 530/388.1

(58) Field of Search ................................ 435/7.23, 325, 435/252.3, 4, 7.1, 7.21, 960, 967; 436/501, 503, 811, 815; 530/388.2, 388.8, 389.1, 389.7, 391.3, 412, 350, 358, 387.1, 387.7, 388.1

(56) References Cited

U.S. PATENT DOCUMENTS
5,688,665 * 11/1997 Massague et al. .

OTHER PUBLICATIONS

American Joint Committee on Cancer (Beahrs et al. (1992). 4th ed. Chicago, American Joint Committee on Cancer, 115–122.

Cordon–Cardo, C., "Mutations of Cell Cycle Regulators. Biological and Clinical Implications for Human Neoplasia", (1995) *Am. J. Pathol.* 147:545–560.

Fero et al., "A Syndrome of Multiorgan Hyperplasia with Features of Gigantism, Tumorigenesis, and Female Sterility in p27$^{Kip1}$–Deficient Mice", (1996) *Cell* 85:733–774.

Kawamata et al. "Molecular Analysis of the Cyclin–dependent Kinase Inhibitor Gene p27/Kip1 in Human Malignancies[1]", (1995) *Cancer Research* 55:2266–2269.

Kiyokawa et al. "Enhanced Growth of Mice Lacking the Cyclin–Dependent Kinase Inhibitor Function of p27$^{Kip1}$", (1996) *Cell* 85:721–732.

Koff et al., Human Cyclin E, a New Cyclin That Interacts with Two Members of the CDC2 Gene Familiy, (1991) *Cell* 66:1217–1228.

MacLachlan et al. "Cyclins, Cyclin–Dependent Kinases and Cdk Inhibitors: Implications in Cell Cycle Control and Cancer", (1995) *Crit. Rev. Eukaryotic Gene Expression* 5(2):127–156.

Mal et al. "Inactivation of p27$^{Kip1}$ by the viral E1A oncoprotein in TGFβ–treated cells", (1996) *Nature* 380:262–265.

Nourse et al., "Interleukin–2 mediated elimination of the p27$^{Kip1}$ kinase inhibitor prevented by rapamycin", (1994) *Nature* 372:570–573.

Pagano et al., "Role of the Ubiquitin–Proteasome Pathway in Regulating Abundance of the Cyclin–Dependent Kinase Inhibitor p27", (1995) *Science* 269:682–685.

Pietenpol et al., "Assignment of the Human p27$^{Kip1}$ Gene to 12p13 and Its Analysis in Leukemias[1]", (1995) *Cancer Research* 55:1206–1210.

Polyak et al. (1994) *Cell* 79: 59–66.

Ponce–Castañeda et al., "p27$^{Kip1}$: Chromosomal mapping to 12p12–12p13.1 and Absence of Mutations in Human Tumors[1]", (1995) *Cancer Research* 55:1211–1214.

Shottenfeld, D., "Epidemiology of lung cancer", in *Lung Cancer: Principles and Practice*, ed. by Pass H.I., Mitchell J.B., Johnson, Turrisi AT. (1996). Lippincot–Raven Publishers, Philadelphia.

St. Croix et al., Impact of the cyclin–dependent kinase inhibitor p27$^{Kip1}$ on resistance of tumor cells to anticancer agents, (1996) *Nature Medicine* 2(11):1204–1210.

Stegmaier et al., "Mutational Analysis of the Candidate Tumor Suppressor Genes TEL amd KIP1 in Childhood Acute Lymphoblastic Leukemia[1]", (1986) *Cancer Research* 56:1413–1417.

Toyoshima, T. and Hunter, T., p27, a Novel Inhibitor of G1 Cyclin–Cdk Protein Kinase Activity, Is Related to p21, (1994) *Cell* 78: 67–74.

Zerfass–Thome et al., "Inactivation of the cdk inhibitor p27$^{Kip1}$ by the human papillomavirus type 16 E7 oncoprotein", (1996) *Oncogene* 2323–2330.

Sclafani, R.A. et al. Cell cycle control and cancer: Lessons from lung cancer. J. Investigative Dermatology Symposium Proceedings 1: 123–127, 1996.*

Steeg and Abrams, "Cancer prognostics: Past, present and p27", *Nature Medicine*, 3:152–154 (1997).

Porter et al., "Expression of cell–cycle regulators p27$^{Kip1}$ and cyclin E, alone and in combination, correlate with survival in young breast cancer patients", *Nature Medicine*, 3:222–225 (1997).

Catzavelos et al., "Decreased levels of the cell–cycle inhibitor p27$^{Kip1}$ protein: Prognostic implications in primary breast cancer", *Nature Medicine*, 3:227–230 (1997).

Loda et al., "Increased proteasome–dependent degradation of the cyclin–dependent kinase inhibitor p27 in aggressive colorectal carcinomas", *Nature Medicine*, 3:231–234 (1997).

Lloyd et al., "Aberrant p27$^{kip\,1}$ Expression in Endocrine and other Tumors", *American Journal of Pathology*, 150;2 (2):401–407 (1997).

(List continued on next page.)

Primary Examiner—Nancy A. Johnson
Assistant Examiner—Anne L. Holleran
(74) Attorney, Agent, or Firm—Seidel, Gonda, Lavorgna & Monaco, PC

(57) ABSTRACT

Methods of grading tumors and prognosticating survival rates of cancer patients by determination of p27 expression levels in tissues samples from tumors are provided.

4 Claims, No Drawings

OTHER PUBLICATIONS

Veillette et al., "Expression of the lck Tyrosine Kinase Gene in Human Colon Carcinoma and other Non–Lymphoid Human Tumor Cell Lines", *Oncogene Research,* 1:357–374 (1987).

Bullrich et al., "Chromosomal Mapping of Members of the cdc2 Family of Protein Kinases, cdk3, cdk6, PISSLRE, and PITALRE, and a cdk Inhibitor, $p27^{kip1}$, to Regions involved in Human Cancer", *Cancer Research* 55:1199–1205 (1995).

Claudio et al., "p130/Rh2 Has Growth Suppressive Properties Similar to yet Distinctive from Those of Retinoblastoma Family members pRb and $p107^1$", *Cancer Res.* 54:5556–5560 (1994).

* cited by examiner

DETERMINATION OF CYCLIN-DEPENDENT KINASE INHIBITOR P27 LEVELS AS A PROGNOSTIC FACTOR IN CANCER PATIENTS

This application claims benefit of priority to provisional application Ser. No. 60/046,529, filed May 15, 1997.

INTRODUCTION

This invention was made in the course of research sponsored by the National Institutes of Health. The U.S. Government may have certain rights in this invention.

BACKGROUND OF THE INVENTION

The eukaryotic cell cycle is controlled by protein complexes composed of cyclins and cyclin-dependent kinases (cdks). The regulatory function of cdks is achieved by phosphorylation of key substrates, such as the members of the retinoblastoma gene family. Activity of cdks is regulated by post-translational modification and by the association or dissociation with inhibitory subunits designated cyclin-dependent-kinase inhibitors (CKIs). Two families of these inhibitors have been identified in mammalian cells. Members of each of the two families share a high percentage of sequence homology, in addition to their specificity of interaction with cdks. The first family, which includes p21 (also known as Cip1, Pic1, Sdi1, mda6 and Waf1), p27 (also known as Ick, Kip1 and Pic2) and p57 (also known as Kip2) preferentially inhibit cdk2. The second family, which includes p16 (also known as Ink4A, Mts1, Cdkn2 and Cdkn4i), p15 (also known as Ink4B and Mts2), p18 (also known as Ink4C and Ink6A) and p19/p20 (also known as Ink4D and Ink6B) preferentially bind to and inhibit cdk4 and cdk6. Results from several studies indicate CKIs to be the products of potential tumor-suppressor genes (MacLachlan et al. (1995) *Crit. Rev. Eukaryotic Gene Expression* 5:127–156).

p27 was first identified in complexes with cdk2/cyclin E in Transforming Growth Factor-β (TGF-β) arrested cells (Koff et al. (1991) *Cell* 66:1217–1228). p27 protein associates with cyclin E/cdk2 and Cyclin A/cdk2 complexes and inhibits their activities. It is a negative cell cycle regulator implicated in G1 phase arrest by TGF-β cell contact, inhibition agents that increase the level of cyclic AMP, staurosporin, lovastatin, tamoxifen and rapamycin. Overexpression of p27 protein in mammalian cells induces a G1 block of the cell cycle (Polyak et al. (1994) *Cell* 79: 59–66; Toyoshima, T. and Hunter, T. (1994) *Cell* 78: 67–74). In addition, high levels of p27 have been found in quiescent cells thus suggesting a role for p27 in maintaining cells in G0 (Nourse et al. (1994) *Nature* 372:570–573). Levels of p27 decrease as cells reenter the cell cycle, mostly due to ubiquitin-proteosome dependent degradation (Pagano et al. (1995) *Science* 269:682–685). No structural alteration of p27 gene has been reported in human neoplasms to date (Bullrich et al. (1995) *Cancer Research* 55: 1199–1205; Cordon-Cardo, C. (1995) *Am. J. Pathol.* 147:1–16; Kawamat et al. (1995) *Cancer Research* 55:2266–2269; Pietenpol et al. (1995) *Cancer Research* 55:1206–1210; Ponce-Castañeda et al. (1995) *Cancer Research* 55:1211–1214; Stegmaier et al. (1996) *Cancer Research* 56:1413–1417). Thus, despite its potential role as a tumor suppressor, p27 gene does not appear to be mutated in human tumors.

However, recent evidence suggests an involvement of this CKI in neoplastic transformation. For example, p27 deficient mice have been shown to develop tumors of the pituitary gland with 100% of penetrance (Fero et al. (1996) *Cell* 85:733–774; Kiyokawa et al. (1996) *Cell* 85:721–732). In addition, p27 has been shown to be a target of the Adenovirus E1A (Mal et al. (1996) *Nature* 380:262–265). Further, HPV E7 oncoproteins have been shown to dissociate p27 from the cyclin/cdk complexes (Zerfass-Thome et al. (1996) *Oncogene* 2323–2330). p27 has also been implicated as a regulator of drug resistance in solid tumors and has been suggested as a target for development of antagonists which may be useful as chemosenstizers in conjunction with conventional anticancer therapy. St. Croix et al. (1996) *Nature Medicine* 2(11):1204–1210.

It has now been found that levels of p27 expression in tumor cells correlate with the degree of malignancy of the tumor and can be used in prognosticating overall survival time in cancer patients.

SUMMARY OF THE INVENTION

An object of the present invention is to provide a method of determining the degree of malignancy or grading of a tumor in a patient by determining levels of p27 expression in tumor cells isolated from the patient.

Another object of the present invention is to provide a method of prognosticating overall survival time in cancer patients by determining levels of p27 expression in tumor cells isolated from the patient.

DETAILED DESCRIPTION OF THE INVENTION

Lung cancer in the greatest single cause of cancer-related deaths in Western countries and despite continuing research efforts into new therapeutic strategies, survival in patients suffering from lung cancer (approximately 13%) has not improved over the past two decades. Only approximately 30% of patients suffering from lung cancer are eligible for radical lung resection, and only about one third of these patients are free from disease 5 years after surgery (Shottenfeld, D., "Epidemiology of lung cancer", in *Lung Cancer: Principles and Practice*, ed. by Pass H. I., Mitchell J. B., Johnson, Turrisi A T. (1996). Lippincot-Raven Publishers, Philadelphia) . Thus, accurate determination of the cancer's malignant potential is important in order to select an appropriate course of therapy.

This determination, known as "grading", is typically carried out by examination of the character and appearance of tumor sections by skilled pathologists and is based upon a number of histological criteria. However, a significant problem in the use of such histological criteria is that they are subjective, and variability exists not only between different pathologists but, oftentimes, within a single pathologist's reading of the same tissue specimen. In addition, there is heterogeneity within the tumor itself in both primary and metastatic sites. Accordingly, there is a need for more accurate determination of the malignant potential of a tumor.

It has now been found that expression levels of cell cycle regulators such as p27 in tumor cells correlate with the degree of malignancy (grading) (p=0.01). Further, expression levels of p27 in tumor cells were shown to correlate with survival time in cancer patients. Thus, a simple immunohistochemical assay measuring p27 expression on formalin fixed-paraffin embedded specimens can now be used to quickly and reproducibly to grade tumor and to evaluate the prognosis of cancer patients.

Accordingly, the present invention provides a method of grading tumors by determination of the levels of p27 expression in a tissue sample from a tumor. Tissue samples of a tumor can be obtained by various means including, but not limited, surgical resectioning or removal and biopsies. Once the tissue is obtained, levels of p27 expression in the sample are determined preferably via an immunohistochemical assay. As will be obvious to those of skill in the art upon this disclosure, however, other means of measuring p27 expression levels in tissues can be used. The levels are then compared to established control levels of p27 expression in normal noncancerous tissue, nonmetastic cancerous tissue and metastic cancerous tissue so that tissue sample can be graded.

The present invention also provides a method for prognosticating the survival rates of cancer patients by determination of p27 levels in tumor tissue obtained from these patients. For example, the determination of p27 levels in tissue samples from patients affected by non small cell lung cancer was demonstrated to have prognostic value in identifying those patients most likely to benefit from radical lung resection. By "non small cell lung cancer or NSCLC", it is meant all forms of lung cancer except small cell lung cancer (SCLC) and includes, but is not limited to squamous cell carcinomas, adenocarcinomas, broncioaveolar carcinomas and large cell carcinomas. p27 protein expression levels were measured in a series of non small cell lung cancer specimens. Immunohistochemistry and western blot analysis were performed on each specimen. Tumors expressing low to undetectable levels of p27 were found to contain high p27 degradation activity. Expression levels were then correlated with the outcomes of these patients. It was found that p27 was a prognostic factor correlating with the overall survival times ($p=0.0012$).

More specifically, routine histological assays were performed on 108 samples of non small cell lung cancers and evaluated independently by p27 immunostaining. Sixty-two of these tumors were identified as adenocarcinomas while 46 were squamous carcinomas. Sixty-two of the tumors (57.4%) were classified as stage I, 18 of the tumors (16.7%) were classified as stage II and 28 tumors (25.9%) were classified as stage III. Thirty-two of the tumors were considered low differentiated (29.6%), 42 of the tumors were medium differentiated (38.9%) and 34 of the tumors were well differentiated (31.5%).

Immunoreactivity for p27 was found in both normal and neoplastic tissues. p27 immunostaining in both tissues was always nuclear, with a low to absent background. p27 expression in normal lung tissue was detected in bronchial epithelia (mostly in ciliated cells) and in the adjacent glands. Pneumocytes displayed moderate nuclear immunoreactivity. p27 immunostaining was also observed in 96 (88.9%) of the neoplastic specimens. The percentage of positive cells in the remaining 12 specimens (11.1%) ranged from 0 to 5%. No statistically significant difference in the p27 expression was found between adenocarcinomas and squamous carcinomas. Specificity of the staining was confirmed by blocking with a p27 specific antibody.

p27 expression was also analyzed in these specimens by western blot. Protein extracts were prepared from all of the 108 frozen samples. p27 protein was found at varying levels in all of the specimens examined. Twelve of the 108 specimens, however, had undetectable levels of p27 protein expression. To confirm that the same amount of protein was present in each lysate and that the samples were not degraded, the same blot was normalized with the monoclonal antibody heat shock protein 72/73 (HSP 72/73; Oncogene Science, Uniondale, N.Y.). Results from western blotting correlated statistically with results from the immunohistochemical assays ($p<0.001$).

Northern blot analysis was performed to determine if the different levels of p27 protein were related to difference in transcriptional levels. However, similar amounts of p27 transcript were found to be present in all the examined specimens.

Accordingly, degradation assays were performed to determine whether the p27 degradation pathway was enhanced in tumors with low to undetectable p27 expression. In these experiments, 1 gram of each frozen human tissue sample (6 representative samples) was sectioned and quickly homogenized at 15000 rpm in 1 ml of ice cold doubly distilled water. The sample was frozen and thawed 3 times. Purified recombinant p27 was incubated either alone or in the presence of extracts from tumor expressing different p27 levels for 1 hour, 3 hours, 6 hours, 9 hours and 12 hours. It was found that tumors with high p27 expression level presented lower degradation activity, as compared with tumors with low or undetectable p27 expression level, which presented high or very high degradation activity. Thus, low levels of p27 protein in tumors correlate with high p27 degradation activity.

The role of proteasome in this degradation was then determined. In these experiments, samples with low to undetectable p27 expression were ultracentrifuged to eliminate the proteosome particles. Purified recombinant p27 was then incubated in the presence of extracts from the proteasome depleted supernatant and in the same supernatant after readdition of the proteasome-rich pellet. No degradation was detected in the sample in which the proteasome was left out. p27 degradation was found to be restored in the sample in which the proteasome was added back to the supernatant.

Specimens were then divided into three groups based upon p27 expression levels. The first group (referred to as non expressors) contained 12 specimens (11.1%) with up to 5% of cells positive for p27. The second group (referred to as low expressors) contained 56 (51.8%) specimens with up to 50% of cells positive for p27. The third group contained 40 specimens (37%) with p27 immunostaining detected in more than 50% of positive cells (referred to as high expressors). Analysis of the data utilizing such necessarily arbitrary cuts-off was highly statistically significant and, therefore, functionally operative. A significant negative relationship was found between p27 expression and the histological grading ($p=0.01$) assigned to the specimen. In addition, p27 expression was associated significantly with overall survival. The median survival time in low expresser patients was 20 months as compared to 30 months in high expressor patients and only 14 months in non expresser patients. The five year survival rate also differed statistically among the three groups ($p=0.0012$). The low expresser group had an overall survival of 14% as compared to 25% for the high expresser group. All 12 non expressor patients were dead within 30 months following surgery. Accordingly, p27 levels served as a prognostic factor correlating with the overall survival time of the patients ($p=0.0012$). This correlation was strengthened by the relationship found between p27 expression levels and the degree of malignancy (grading) ($p=0.01$).

Similar results have been obtained for p27 in a cohort of one hundred and forty-nine patients with carcinoma of the colon or rectum. Accordingly, in addition to non small cell lung cancer, the determination of p27 expression levels can be used in grading of other types of tumors and in prognosticating survival rates in cancer patients suffering from these tumors.

The following nonlimiting examples are being provided to further illustrate the present invention.

EXAMPLES

Example 1

Population study

One hundred and eight non small cell lung cancer specimens were obtained from patients who underwent a surgical resection (lobectomy or pneumonectomy) in the departments of Thoracic Surgery of the V. Monaldi Hospital and of the II University of Naples (Italy) between 1988 and 1992. All specimens were from patients who had not received chemo- or radio-therapy prior to surgical resection. Outcome data were collected from hospital charts and from periodic interviews with patients and their relatives. The follow up period was 48 months from the date of surgery (for survivors). Patients who died of causes other than lung cancer were not included in the study. The mean age was 60.1. Gender was unevenly distributed with females accounting for only 7.4% of the population (8 patients). The histological diagnoses and classifications of the tumors were based on the WHO criteria (World Health Organization, 1981). The postsurgical pathologic TNM stage was determined according to the guidelines of the American Joint Committee on Cancer (Beahrs et al. (1992). 4th ed. Chicago, American Joint Committee on Cancer, 115–122). After surgical resection each tumor specimen was divided into two parts. The first part was frozen instantly for the extraction of RNAs and proteins. The second part was formalin fixed immediately and then paraffin embedded for routine and immunohistochemical investigation.

Example 2

Immunohistochemistry

Immunohistochemistry sections from each specimen were cut at 3–5 µm, mounted on glass and dried overnight at 37° C. All sections were deparaffinized in xylene, rehydrated through a graded alcohol series and washed in PBS. This buffer was used for all subsequent washes and for dilution of the antibodies. Sections were heated twice in a microwave oven for 5 minutes, each at 700 W, in 10 mmole/L citrate buffer (pH 6); sequentially quenched in 0.5% hydrogen peroxide; and blocked with diluted 10% normal horse anti-mouse serum (Vector Laboratories, Burlingame, Calif.). A monoclonal antibody raised against p27 (Transduction Laboratories) was used (dilution 1:100). The incubation time was 60 minutes at room temperature. After washing in PBS, slides were incubated with diluted horse anti-mouse biotinylated antibody (Vector Laboratories) for 30 minutes at room temperature. All slides were processed by the ABC method (Vector Laboratories) for 30 minutes at room temperature. Diaminobenzidine was used as the final chromogen, and hematoxylin was used as the nuclear counterstain. To evaluate the specificity of the antibody, the protein used to generate it and an irrelevant protein were both pre-adsorbed to the antibody. Negative controls for each tissue section were prepared by leaving out the primary antibody. Immunohistochemistry was performed on normal bronchial specimens to establish the normal p27 expression pattern of this tissue for use as the positive control. All samples were processed under the same conditions. The staining pattern of the protein was evaluated and scored for the percentage of positive nuclei by two separate pathologists: a score of 1 refers to less than 10% positive cells; a score of 2 refers to a range of from 10% to 50% positive cells; and a score of 3 refers to more than 50% positive cells. At least 20 high power fields were chosen randomly and 2000 cells were counted.

Example 3

Western Blot

One gram of each frozen lung cancer tissue sample was sectioned and quickly homogenized at 4° C. in 250 mM NaCl, 50 mM Tris (pH 7.4), 5 mM EDTA, 0.1% (v/v) Triton X-100, 1 mM phenylmethylsulfonyl fluoride, 50 mM NaF, 0.5 mM $Na_3VO_4$, 10 mg/ml leupeptin and 50 mg/ml aprotinin. The homogenates were then spun at 13,000×g at 4° C. and total protein in the extracts was determined. Fifty milligrams of protein was denatured by boiling in 2× Laemmli sample buffer and separated by electrophoresis in a 15% sodium dodecyl sulfate-polyacrylamide gel, followed by electrophoretic transfer of the proteins to a PVDF membrane (Millipore, Bedford, Mass.) in CAPS buffer (10 mM CAPS, 20% methanol, pH 11). The membrane was then blocked with 5% milk in TBS-T buffer (2 mM Tris, 13.7 mM NaCl, 0.1% Tween-20, pH 7.6) and washed in TBS-T. Primary antibody was incubated with the membrane in 3% milk and then washed in TBS-T. Sheep anti-mouse antibody coupled to horseradish peroxidase was incubated with the membrane and then washed in TBS-T. The presence of secondary antibody bound to the membrane was detected using the ECL system (Dupont NEN, Boston, Mass.).

Example 4

Northern Blot Analysis

Cytoplasmic RNA was extracted using the RNAzol method (CINNA/BIOTECX, Friendswood, Tex.) after homogenization from 13 non small cell lung cancer samples (including samples representative of all the coded p27 expressing groups). Northern blots were performed in accordance with procedures described by Claudio et al. (1994). *Cancer Res* 54: 5556–5560.

Example 5

Degradation assay

One gram of each frozen human tissue sample (6 representative samples) was sectioned and quickly homogenized at 15,000 rpm in 1 ml of ice cold doubly distilled water. The sample was frozen and thawed 3 times. The lysate was spun down at 15,000 rpm for 45 minutes at 4° C. The supernatant was retrieved and frozen at −80° C. This method of preparation of total extract preserves ubiquitinating enzymes. Purified histidine-tagged p27 (0.06 ml) was incubated at 37° C. for various time periods in 30 ml of degradation mix containing 100 mg of protein human tissue extracts, 50 mM Tris-HCL (pH 8.0), 5 mM $MgCl_2$, and 1 mM DTT, 2 mM ATP, 10 mM creatine phosphate and 5 mM ubiquitin. Degradation of p27 was analyzed by immunoblotting with p27 mAb. In order to remove the proteasome, tumor samples were ultracentrifuged at 100,000 g for 6 hours in accordance with procedures described by Pagano M et al. (1995) *Science* 269: 682–685.

Example 6

Statistical analysis

Patient survival data were used to determine a correlation between p27 expression levels and overall survival time. Survival curves were constructed using Kaplan-Meier analysis. Statistical significance of these data was measured by the Mantel-Cox test. Possible associations between the different variables of the analyzed tumor samples were tested by the chi square test.

What is claimed is:

1. A method of grading a tumor comprising:
   (a) obtaining a tissue sample from a tumor;
   (b) measuring a level of p27 protein in the tissue sample;

(c) comparing the measured p27 protein level to established control levels of p27 protein; and (d) assigning a pathological grade to the tumor based upon the level of p27 protein in the tissue sample.

2. The method of claim 1 wherein the tumor comprises non small cell lung cancer.

3. A method of prognosticating a survival time of a cancer patient comprising:

(a) obtaining a tissue sample from a tumor of a cancer patient;

(b) measuring a level of p27 protein in the tissue sample; and (c) predicting a survival time of the cancer patient based upon the measured level of p27 protein, said protein level being indicative of patient survival time.

4. The method of claim 3 wherein the cancer patient is suffering from non small cell lung cancer.

* * * * *